United States Patent
Sit

(10) Patent No.: US 7,091,212 B2
(45) Date of Patent: Aug. 15, 2006

(54) CHIRAL DINAPSOLINE

(75) Inventor: Sing-Yuen Sit, Meriden, CT (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/398,116

(22) PCT Filed: Aug. 8, 2002

(86) PCT No.: PCT/US02/25267

§ 371 (c)(1),
(2), (4) Date: Apr. 2, 2003

(87) PCT Pub. No.: WO03/013532

PCT Pub. Date: Feb. 20, 2003

(65) Prior Publication Data

US 2004/0063741 A1     Apr. 1, 2004

Related U.S. Application Data

(60) Provisional application No. 60/311,614, filed on Aug. 10, 2001.

(51) Int. Cl.
*C07D 221/18*     (2006.01)
*A61K 31/44*     (2006.01)

(52) U.S. Cl. ........................ 514/284; 546/61
(58) Field of Classification Search .................. 546/61; 514/284

See application file for complete search history.

(56) References Cited

U.S. PATENT DOCUMENTS 5,047,536 A    9/1991  Nichols ........................ 546/61
5,420,134 A    5/1995  Nichols et al. ............. 514/280

FOREIGN PATENT DOCUMENTS

| WO | WO 97/02513 | 2/1996 |
| WO | WO 97/06798 | 2/1997 |
| WO | WO 97/06799 | 2/1997 |
| WO | WO 02/13827 A1 | 2/2002 |

OTHER PUBLICATIONS

D. Ghosh, et al., *J. Med. Chem.* 39: 549-555 (1996).
R. Mattson, et al., *ACS Organic Division*, Boston Abstract No. 059 (1998).
C.P. Manik, et al., *J. Neurochemistry*, 51: 391-397 (1988).
K.D. Burris, et al., *Neuropsychopharmacology*, vol. 12, pp. 335-345 (1995).
Remington's Pharmaceutical Sciences, Mack Publishing Comp., Easton, P.A. 17th edition, 1985.
Pearson, et al., in *J. Heterocycl. Chem* ., vol. 6(2), pp. 243-245 (1969).
Sing-Yuen Sit et al., "(+) Dinapsoline: An Efficient Synthesis and Pharmacological Profile of a Novel Dopamine Agonist", *Journal of Medicinal Chemistry*, vol. 45, No. 17, pp. 3660-3668, (2002).

*Primary Examiner*—Zinna N. Davis
(74) *Attorney, Agent, or Firm*—Barnes & Thornburg LLP

(57) ABSTRACT

The present invention relates to the preparation of the optical isomer (R)-(+)-8,9-dihydroxy-2,3,7,11b-tetrahydro-1H-napth[1,2,3-de]isoquinoline. This invention also relates to the use of pharmaceutical compositions comprising (R)-(+)-8,9-dihydroxy-2,3,7,11b-tetrahydro-1H-napth[1,2,3-de]isoquinoline for use for the treatment of movement disorders.

4 Claims, No Drawings

CHIRAL DINAPSOLINE

CROSS-REFERENCE TO RELATED APPLICATIONS

This application is a U.S. national counterpart application of international application Ser. No. PCT/US02/25267 filed Aug. 8, 2002, which claims priority to U.S. provisional application Ser. No. 60/311,614 filed Aug. 10, 2001.

FIELD OF THE INVENTION

The present invention relates to the optically active (+) isomer of dinapsoline which, illustratively, is useful as a dopamine receptor agonist in the treatment of movement disorders.

BACKGROUND OF THE INVENTION

Dopamine has been implicated in numerous neurological disorders. It is generally recognized that either excessive or insufficient functional dopaminergic activity in the central and/or peripheral nervous system may cause hypertension, narcolepsy, and other behavioral, neurological, physiological, and movement disorders including Parkinson's disease, a chronic, progressive disease characterized by an inability to control the voluntary motor system.

A number of ligands for the treatment of dopamine-related dysfunction of the central and peripheral nervous system are described in U.S. Pat. No. 5,047,536 issued Sep. 10, 1991, U.S. Pat. No. 5,420,134 issued May 30, 1995, and International Publication WO 96/02513 published Feb. 1, 1996. Furthermore, International Publication WO 97/06798, published Feb. 27, 1997, describes compounds having the general tetrahydro-1H-napth[1,2,3-de]isoquinoline chemical structure described below.

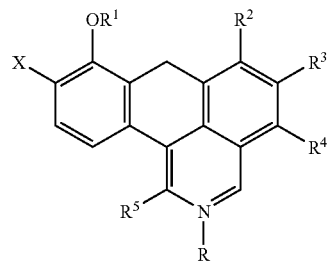

In particular, International Publication WO 97/06799 specifically describes the synthesis and use of (±)-8,9-dihydroxy-2,3,7,11b-tetrahydro-1H-napth[1,2,3-de]isoquinoline denominated as "dinapsoline" in the description. The synthesis of dinapsoline is depicted generally in FIGS. 1 and 2 as well as in the experimental section. Further description of the synthesis and pharmacological evaluation of dinapsoline is described by D. Ghosh, et al. in *J. Med. Chem.*, Vol. 39, pp. 549–555 (1996).

However, neither publications contains a description of the stereoisomers of dinapsoline or their potential pharmacological behavior. Although there is some speculation that the possible activities may reside in one enantiomer, there are no actual examples or biological data presented.

SUMMARY OF THE INVENTION

The present invention relates to the preparation of the optical isomer (R)-(+)-8,9-dihydroxy-2,3,7,11b-tetrahydro-1H-napth[1,2,3-de]isoquinoline and its use, illustratively for the treatment of movement disorders.

DETAILED DESCRIPTION OF THE INVENTION

The present invention relates to new enantiomer of dinapsoline which is chemically known as (R)-(+)-8,9-dihydroxy-2.3,7,11b-tetrahydro-1H-napth[1,2,3-de]isoquinoline.

The preparation of dinapsoline is described by D. E. Nichols, et al. in International Publication WO 97/06799, published Feb. 27, 1997. However, a preferred method of preparation is illustrated in Reaction Schemes 1 and 2 as well as in the Examples described herein.

The compound of Formula VIII may be prepared by various procedures, such as those illustrated herein in the examples, in the Reaction Schemes and variations thereof which would be evident to those skilled in the art. The fused isoquinolines of Formula VIII advantageously may be prepared by reduction methods from benzo benzoisoquinoline compounds of Formula VII followed by removal of the hydroxy-protecting group as illustrated in Reaction Scheme 2. The benzo benzoisoquinolines of Formula VII advantageously may be prepared using free radical carbon-carbon bond formation from aryl isoquinolines of Formula VI as illustrated in Reaction Scheme 2, while the aryl isoiquinolines of Formula V may be prepared from isoquinolines of Formula I by the method illustrated in Reaction Scheme I.

REACTION SCHEME 1

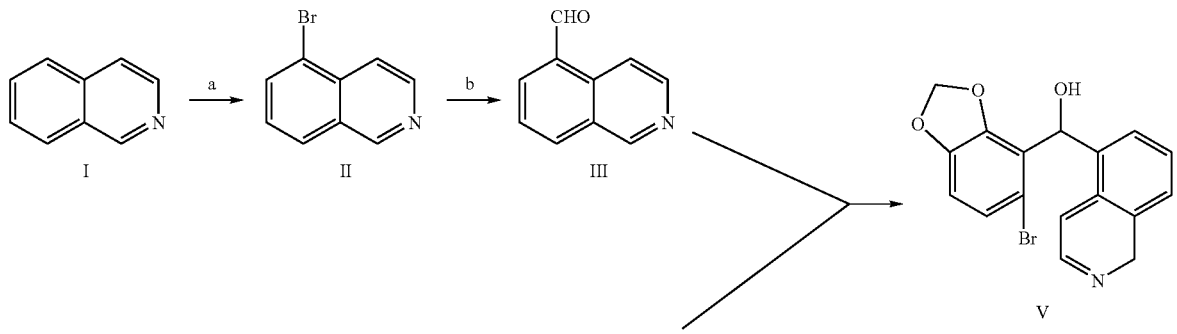

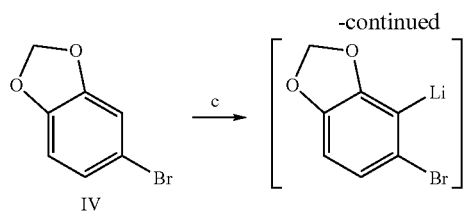

IV

Reagents: (a) Br$_2$/AlCl$_3$/neat; (b) n-BuLi then DMF; (c) LDA then III.

As illustrated in Reaction 1, the compound of Formula V may be prepared from the isoquinoline of the Formula I, which is generally known to undergo electrophilic substitution preferentially at the 5-position to give 5-bromo-isoquinoline of the Formula II. The bromination reaction (a) illustratively can be done in neat form and in the presence of a Lewis Acid catalyst such as anhydrous aluminum chloride, or alternatively, the bromination can be carried out in an inert organic solvent such as methylene chloride. In both cases, the overall yields are comparable to each other, and illustratively, the bromination is carried out in neat form since it avoids the additional solvent evaporation step. The 5-bromo-isoquinoline compound of Formula II can be transmetallated to the corresponding 5-lithio-isoquinoline using n-butyl lithium in a suitable inert organic solvent such as THF and the reaction is preferably carried out, at a temperature below −50 to −80° C. This versatile 5-lithio-isoquinoline can be alkylated, acylated into a variety of 5-substituted isoquinolines. With the addition of DMF to the 5-lithio-isoquinoline followed by warming to room temperature and neutralization with an equivalent amount of mineral acid, this 5-lithio-isoquinoline produced the 5-formyl-isoquinoline of Formula III in excellent yields. Using a recently published procedure described by R. Mattson, et al., in *ACS Organic Division,* 1998, Boston Abstract No. 059, the aldehyde of Formula III advantageously may be reacted with the 4-bromo-3-lithio-1,2-(methylenedioxy)benzene derived from the corresponding hydrocarbon precursor of Formula IV to furnish the desired benzhydrol of Formula V, in crystalline form.

The cyclization of the compound of Formula V to the corresponding compounds of Formulas VI can be initiated by a variety of reaction conditions well-known to those skilled in the art. However, it was found that good results were achieved by free radical initiated carbon-carbon bond formation, since this method was the least sensitive to the electronic environment of the selected precursor. The carbon-carbon bond reaction is illustratively carried out with a hydrogen radical source such as trialkyltin hydride, triaryltin hydride, trialkylsilane, triarylsilane, or the like and a radical initiator such as 2,2'-azobisisobutylronitrile, sunlight, controlled potential cathodic (Pt), or the like in the presence of a proton source such as a mineral acid; for example, sulfuric acid and hydrochloric acid or an organic acid, for example, acetic acid, trifluoroacetic acid and p-toluenesulfonic acid. In the conversion of compound of Formula V to the cyclized compound of Formula VI, it is advantageous to use tributyltin hydride with a variety of well-known initiators and specifically, 2,2'-azobisisobutylronitrile in the presence of acetic acid.

REACTION SCHEME 2

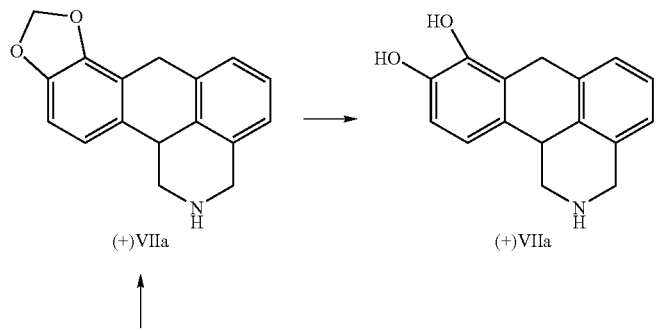

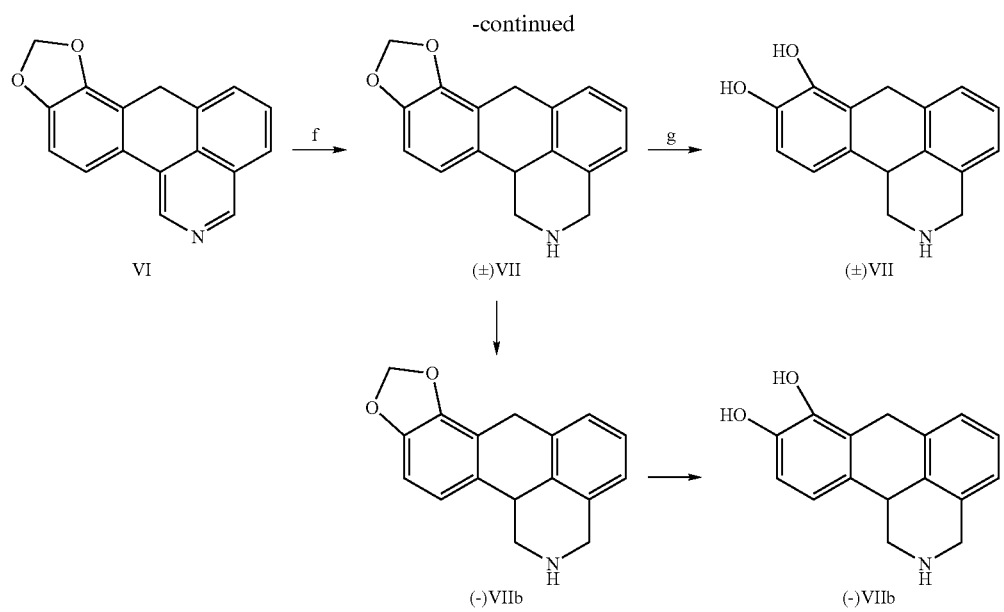

Reagents: (f) NaBH$_3$CN in HCl/THF; (g) BBr$_3$/CH$_2$Cl$_2$

Once cyclized, the compound of Formula VI is selectively reduced at the nitrogen bearing heterocyclic ring to give the corresponding tetrahydroisoquinoline of Formula VII, the direct precursor of dinapsoline of Formula VIII. The selective ring reduction may be carried out by a number of different reduction methods such as sodium cyanoborohydride in an acidic medium in THF, hydride reducing agents such as L-Selectride® or Superhydride®, and catalytic hydrogenation under elevated pressure may be employed. Conversion of the protected compound of Formula VII to the diol of Formula VIII may be accomplished by using boron tribromide in methylene chloride at low temperatures such as −60 to −80° C. and the final product may be isolated in the form of a hydrobromide salt. The corresponding hydrochloride salt may be prepared by using boron trichloride.

According to the present invention, the substantially pure (+)-isomer of dinapsoline VIIIa is prepared by chiral separation of the hydroxy-protected racemic dinapsoline (±)VII followed by removal of the protecting group in compound (+)VIIa to afford the desired pharmacologically active (+)-dinapsoline isomer of Formula (+)VIIIa. In addition, the same chiral (+)-isomer of Formula VIIIa is obtained by chemical resolution using (+)-dibenzoyl-D-tartaric acid by the hydroxyprotected racemic dinapsoline followed by removal of the protecting group to afford the same optically active isomer.

It should be appreciated by those skilled in the art that the (−)-isomer of dinapsoline can be prepared from the isolated compound of Formula (−)VIIb using the same physical and chemical resolution methods.

Binding to Dopamine Receptors:

Dopamine produces biological responses through stimulation of its receptors on cell membranes. The affinity for D1 and D2 receptors was carried out in rat striatum using the in vitro binding assay adapted from C. P. Manik, et al., in J. of Neurochemistry, Vol. 51, pp. 391–397 (1988) and K. D. Burris, et al., in Neuropsychopharmacology, Vol. 12, pp. 335–345 (1995). In addition, membranes prepared from HEK-293 cells that express transfected human D2L receptors, sites labeled by the D2 receptor agonist [125I]-7-OH-PIPAT, were used and the results are provided in Table 1.

TABLE 1

| | Ki (nM) | | |
|---|---|---|---|
| | hD$_{2L}$ receptors in HEK-293 [$^{125}$I]-7-OH-PIPAT | D$_2$ receptors in rat striatum [$^{125}$I]-7-OH-PIPAT | D$_1$ receptors in rat striatum [$^{125}$I]-SCH-23982 |
| (+)-Dinapsoline | 3 | 43 | 48 |
| (−)-Dinapsoline | 168 | 589 | 4550 |
| (+/−)-Dinapsoline | 5 | 50 | 34 |

The results of the above in vitro D$_1$ and D$_2$ binding studies demonstrate that the chiral (+)-dinapsoline of the present invention bound with high affinity to rat and human receptors, but the (−)-enantiomer did not bind with high affinity. Thus, the chiral (+)-dinapsoline of the present invention is useful for the treatment of movement disorders such as, but not limited to, Parkinson's disease, Parkinson-like diseases; depression, obesity, narcolepsy, and drug addiction and/or abuse, for example cocaine addiction and/or abuse.

In one embodiment, a compound is provided which is (R)-(+)-8,9-dihydroxy-2,3,7,11b-tetrahydro-1H-napth[1,2,3-de]isoquinoline or a nontoxic pharmaceutically acceptable salt thereof, the compound (R)-(+)-8,9-dihydroxy-2,3,7,11b-tetrahydro-1H-napth[1,2,3-de]isoquinoline provided in substantially pure form.

In another embodiment, pharmaceutical compositions are provided comprising (R)-(+)-8,9-dihydroxy-2,3,7,11b-tetrahydro-1H-napth[1,2,3-de]isoquinoline in combination with a pharmaceutical adjuvant, carrier, or diluent.

In still another embodiment, this invention relates to a method for the treatment of movement disorders in a mammal in need thereof, which comprises administering to said mammal a therapeutically effective amount of (R)-(+)-8,9-dihydroxy-2,3,7,11b-tetrahydro-1H-napth[1,2,3-de]isoquinoline or a nontoxic pharmaceutically acceptable salt, solvate, or hydrate thereof.

In yet another embodiment, this invention relates to a method for treating an ischemic condition in a mammal, which comprises administering to said mammal a therapeutically effective amount of a compound of Formula I or a non-toxic pharmaceutically acceptable salt, solvate, or hydrate thereof.

For therapeutic use, the pharmacologically active (R)-(+)-8,9-dihydroxy-2,3,7,11b-tetrahydro-1H-napth[1,2,3-de]isoquinoline will normally be administered as a pharmaceutical composition comprising as an essential active ingredient at least one such compound in association with a solid or liquid pharmaceutically acceptable carrier, and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous), bronchial, or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents, and the like. The tablet may, if desired, be film coated by conventional techniques. If a liquid carrier is employed, the preparation may be In the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicles (including edible oils), preservatives, as well as flavoring and/or coloring agents. For parenteral administration, a vehicle illustratively will comprise sterile water, although saline solutions, glucose solutions, and like may be used. Injectable suspensions also may be used, in which case conventional suspending agents may be employed. Conventional preservatives, buffering agents, and the like also may be added to parenteral dosage farms. Particularly useful is the administration of (R)-(+)-8,9-dihydroxy-2,3,7,11b-tetrahydro-1H-napth[1,2,3-de]isoquinoline directly in parenteral formulations. The pharmaceutical compositions are prepared by conventional techniques appropriate to the desired preparation containing appropriate amounts of the active ingredient, that is, the compound according to the invention. See, for example, *Remington's Pharmaceutical Sciences*, Mack Publishing Company, Easton, Pa., 17$^{th}$ edition, 1985.

The therapeutic dosage of (R)-(+)-8,9-dihydroxy-2,3,7,11b-tetrahydro-1H-napth[1,2,3-de]isoquinoline will depend not only on such factors as the age, weight, and sex of the patient and mode of administration, but also on the degree of potassium channel activating activity desired and the potency of the particular compound being used for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of (R)-(+)-8,9-dihydroxy-2,3,7,11b-tetrahydro-1H-napth[1,2,3-de]isoquinoline or pharmaceutical composition thereof for a mammal, including man, suffering from, or likely to suffer from any condition as described herein is an amount of active ingredient from about 0.1 µg/kg to 100 mg/kg body weight. For parenteral administration, the dose may be in the range of 1 µg/kg to 10 mg/kg body weight for intravenous administration. The active ingredient illustratively will be administered in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the invention.

DESCRIPTION OF SPECIFIC EMBODIMENTS

All new compounds reported displayed spectral characteristics (IR, MS, 1H and 13C NMR) which were consistent with their assigned structures. NMRs were run in the indicated solvent [deuterochloroform (CDCl3) or perdeuterodimethylsulfoxide (DMSO-d6)] at 300 MHz using a Bruker ACP 300 q=quartet, p=pentuplet, and br=broadened), integration and coupling constant (given in Hz). Melting points were obtained using a Thomas Hoover capillary apparatus and are uncorrected.

EXAMPLE 1

5-Bromoisoquinoline

The apparatus was a 500 mL three-necked flask equipped with a condenser, dropping funnel, and a stirrer terminating in a stiff, crescent-shaped Teflon polytetrafluroethylene paddle. To the isoquinoline (57.6 g, 447 mmol) in the flask was added $AlCl_3$ (123 g, 920 mmol). The mixture was heated to 75–85° C. Bromine (48.0 g, 300 mmol) was added using a dropping funnel over a period of 4 hours. The resulting mixture was stirred for one hour at 75° C. The almost black mixture was poured into vigorously hand-stirred cracked ice. The cold mixture was treated with sodium hydroxide solution (10 N) to dissolve all the aluminum salts as sodium aluminate and the oily layer was extracted with ether. After being dried with $Na_2SO_4$ and concentrated, the ether extract was distilled at about 0.3 mm. A white solid (16.3 g, 78 mmol) from a fraction of about 125° C. was obtained (26% yield). The product was further purified by recrystallization (pentane or hexanes): mp 80–81° C.;

$^1$H-NMR(DMSO-$d_6$)δ 9.34 (s, 1H), 8.63 (d,1H,J=9.0H$_z$), 8.17 (d,1H,J=7,5Hz), 8.11 (d, 1H, J=6.6 Hz), 7.90 (d, 1H, J=6.0 Hz), 7.60 (t, 1H, J=7.5 Hz);

$^{13}$C NMR (DMSO-$d_6$) δ 153.0, 144.7, 134.3, 134.0, 129.3, 128.5, 128.0, 120.3, and 118.6.

Anal. Calcd. for $C_9H_6BrN$: C, 51.96; H, 2.91; N, 6.73. Found: C, 51.82; H, 2.91; N, 6.64.

EXAMPLE 2

5-Isoquinolinecarboxaldehyde

To a solution of n-butyllithium (19.3 mL of 2.5 M in hexanes, 48 mmol) in a mixture of ether (80 mL) and THF (80 mL) at –78° C. was added dropwise a solution of bromoisoquinoline (5.0 g, 24 mmol) in THF (10 mL). The reaction mixture was stirred at –78° C. under argon for 30 minutes. Following the general procedures described by Pearson, et al., in *J. Heterocycl. Chem.*, Vol. 6 (2), pp. 243–245 (1969), a solution of DMF (3.30 g, 45 mmol) in THF (10 mL) was cooled to –78° C. and quickly added to the isoquinolyllithium solution. The mixture was stirred at –78° C. for 15 minutes. Ethanol (20 mL) was added followed by saturated $NH_4Cl$ solution. The resulting suspension was warmed to room temperature. The organic layer, combined with the ether extraction layer, was dried over $Na_2SO_4$. A pale yellow solid (2.4 g, 15 mmol, 64% yield) was obtained from chromatography ($SiO_2$ Type-H, 50% EtOAc in hexanes) and recrystallization (ethanol): mp 114–116° C.;

$^1$H NMR (DMSO-$d_6$) δ 10.40 (s, 1H), 9.44 (s, 1H), 8.85 (d, 1H, J=6.0 Hz), 8.69(d, 1H, J=6.0 Hz), 8.45 (m, 2H), 7.90 (t, 1H, J=7.2 Hz);

$^{13}$C NMR (DM50-$d_6$) δ 194.23, 153.5, 146.2, 140.2, 135.2, 132.6, 130.2, 128.6, 127.5, and 117.2.

Anal. Calcd. for $C_{10}H_7NO.0.05 H_2O$: C, 75.99; H, 4.53; N, 8.86. Found: C, 75.98; H, 4.66; N, 8.68.

EXAMPLE 3

α-(5-BRomo-1,3-benzodioxol-4-yl)-5-isoquinolinemethanol

To a solution of 4-bromo-1,2-(methylendioxy)benzene (3.01 g, 15 mmol) in THF (20 mL) at –78° C. was added dropwise lithium diisopropylamide (10.6 mL of 1.5 M in cyclohexane, 16 mmol). The reaction mixture was stirred at –78° C. under argon for 20 minutes. A brown solution was formed. A solution of 5-isoquinolinecarboxaldehyde (1.90 g, 12 mmol) in THF (4 mL) was added dropwise. The resulting mixture was stirred at –78° C. for 10 minutes and warmed to room temperature. Stirring was continued for 30 minutes at room temperature, and then the mixture was quenched with saturated $NH_4Cl$ solution. The product was extracted with EtOAc and the solvent was removed under reduced pressure. Chromatography ($SiO_2$ Type-H, 35% EtOAc in Hexanes) of the residue yielded the title compound as a yellow solid (2.8 g, 7.8 mmol, 65% yield): mp 173–175° C.;

$^1$H NMR (DMSO-$d_6$) δ 9.32 (s, 1H), 8.47 (d, 1H, J=6.0 Hz), 8.05 (d, 1H, J=8.1 Hz), 7.96 (d, 1H, J=7.2 Hz), 7.76 (d, 1H, J=6.0 Hz), 7.66 (t, 1H, J=7.8 Hz), 7.14 (d, 1H,=8.1 Hz), 6.84 (d, 1H, J=8.1 Hz), 6.58 (d, 1H, J=8.1 Hz), 6.28 (d, 1H, J=5.4 Hz), 5.95 (s, 1H), 5.80 (s, 1H);

$^{13}$C NMR (DMSO-$d_6$) δ 153.1, 147.6, 147.0, 142.9, 136.9, 132.7, 128.9, 128.3, 127.3, 126.7, 125.6, 124.4, 116.3, 114.0, 109.3, 101.6, and 69.0.

Anal. Calcd. for $C_{17}H_{12}BrNO_3$: C, 57.01; H, 3.38; N, 3.91. Found: C, 57.04; H, 3.51; N, 3.89.

EXAMPLE 4

5-[(5-Bromo-1,3-benzodioxol-4-yl)methyl]isoquinoline

To a solution of secondary alcohol α-(5-bromo-1,3-benzodixol-4-yl)-5-isoquinolinemethanol (8.37 mmol) in trifluoroacetic acid (100 mL), triethylsilane (83.7 mmol) was added and the resulting solution was refluxed for an hour at 70–75° C. and stirred overnight at room temperature. The solvent was removed under vacuum and the residue was dissolved in ethyl acetate, washed with saturated $NH_4Cl$ dried over $Na_2SO_4$, filtered, and concentrated. Purification was performed by column chromatography to afford the trifluoroacetate salt of the title compound as a white crystalline solid (67% yield): mp 138–140° C.;

$^1$H NMR (CDCl$_3$) δ 9.64 (s, 1H), 8.63 (d, 1H, J=6.59 Hz), 8.45 (d, 1H, J=6.62 Hz), 8.14 (d, 1H, J=8.22 Hz), 7.77 (t, 1H, J=7.39 HZ), 7.64 (d, 1H, J=7.29 Hz), 7.13 (d, 1H, J=8.33 Hz), 6.71 (d, 1H, J=8.31 Hz), 5.94 (s, 2H), 4.53 (s, 2H);

$^{13}$C NMR (CDCl$_3$) δ 147.8, 147.7, 147.1, 137.2, 135.1, 134.7, 133.4, 130.3, 128.6, 128.3, 125.9, 120.7, 119.4, 116.3, 109.1, 101.2 and 31.7.

Anal. Calcd. for $C_{17}H_{12}BrNO_2.C_2HF_3O_2$: C, 50.02; H, 2.87; Br, 17.51; N, 3.07. Found: C, 49.91; H, 3.02; Br, 17.95; N, 3.04.

EXAMPLE 5

12H-Benzo[d,e][1,3]benzodioxol[4,5-h]isoquinoline

Method A:

A solution of 5-[(5-bromo-1,3-benzodioxol-4-yl)methyl]-isoquinoline (0.357 g, 1.0 mmol) and 2,2'-azobisisobutylronitrile (0.064 g, 0.39 mmol) in benzene (10 mL) was cooled to –78° C., degassed four times with $N_2$ and then heated to 80° C. under argon. A solution of tributyltin hydride (1.14 g, 3.9 mmol) in 10 ML of degassed benzene was added in two hours. TFA (0.185 g, 1.6 mmol) was added in four equal portions (½ each half hour). The reaction mixture was stirred at 80° C. under argon for six hours after addition of TFA. Additional tributyltin hydride (0.228 g, 0.80 mmol) was added dropwise. The stirring continued overnight (16 hours). Another 2,2'-azobisisobutylronitrile (0.064 g, 0.39 mmol) and TFA (0.093 g, 0.80 mmol) were added in one portion. A solution of tributyltin hydride (1.14 g, 3.9 mmol) in 10 mL of degassed benzene was also added in two hours. More TFA (0.185 g, 1.6 mmol) was added in four equal portions (¼ each half hour). The stirring continued for another six hours and tributyltin hydride (0.456 g, 1.6 mmol) was added dropwise. The reaction mixture was stirred overnight (16 hours). The solvent was removed under reduced pressure. Pentane (100 mL) was added to the residue and the resulting mixture was cooled to –78° C. A brown gum was formed and filtered. The filtrate was extracted with MeCN. The MeCN layer was combined with the brown gum. The crude product from evaporation of MeCN was purified by chromatography ($SiO_2$ Type-H, 15% EtOAc in hexanes). The isolated compound was dissolved in $CH_2Cl_2$ and extracted with HCl (1N). The aqueous layer was basified to pH~10 using 10 N NaOH solution and reextracted with $CH_2Cl_2$. The organic layer was dried over $Na_2SO_4$. Evaporation of solvent yielded the title compound as an orange solid (0.068 g, 0.26 mmol, 25% yield): mp 194–197° C.;

$^1$H NMR (DMSO-$d_6$) δ 9.12 (s, 1H), 9.06 (s, 1H), 7.93 (d, 1H, J=6.9 Hz), 7.83 (d, 1H, J=8.1 Hz), 7.73 (dd, 1H, J=7.2, 1.5 Hz), 7.66 (t, 1H, J=7.8 Hz), 6.96 (d, 1H, J=8.4 Hz), 6.14 (s, 2H), 4.44 (s, 2H);

$^{13}$C NMR (DMSO-$d_6$) δ 150.6, 147.0, 145.2, 135.6, 130.6, 129.3, 129.1, 127.7, 127.5, 125.0, 123.6, 117.2, 116.1, 107.5, 101.6, and 26.6.

Anal. Calcd. for $C_{17}H_{11}NO_2.0.12CH_2Cl_2$: C, 75.75; H, 4.17; N, 5.16. Found: C, 75.75; H, 4.03; N, 4.83.

Method B:

A solution of 5-[(5-bromo-1,3-benzodioxol-4-yl)methyl]-isoquinoline (12.6 g, 36.8 mmol) and 2,2'-azobisisobutylronitrile (5.92 g, 36.0 mmol) in benzene (1500 mL) was cooled to –78° C., degassed/purged four times with nitrogen and then heated to 80° C. under argon. A solution of tributyltin hydride (39.9 g, 137 mmol) in 30 mL of degassed benzene was added dropwise over a period of three hours. Acetic acid (12.5 g, 210 mmol) was added in one portion before the addition of tin hydride. The reaction mixture was stirred at 80° C. under argon for 16 hours. Excess triethylamine was added to neutralize the residual acetic acid component. The solvent was removed under reduced pressure. Methylene chloride (250 mL) was added to dissolve the semi-solid, followed by the addition of hexanes to a point just before the mixture became cloudy. This solution was poured over a short bed of silica gel and the tri-n-butyltin acetate was removed by washing with hexanes until no longer detected by TLC. The product was then eluted out with mixtures of hexanes and ethyl acetate to give the desired title compound (6.1 g, 23.4 mmol, 63.5% yield) which was identical to the product prepared by Method A.

EXAMPLE 6

(±)-8,9-Methylenedioxy-2,3,7,11b-tetrahydro-1H-napht[1,2,3-de]isoquinoline

Method A:

To a solution of 12H-benzo[d,e][1,3]benzodioxol[4,5-h]isoquinoline (0.085 g, 0.33 mmol) in THF (43 mL) was added 2N HCl (1.7 mL, 3.4 mmol) and an orange precipitate formed. Sodium cyanoborohydride (0.274 g, 44 mmol) was added in one portion. The resulting suspension was stirred at room temperature for two hours. HCl (2N, 10 mL) was added and stirring continued for 5 minutes. Saturated $NaHCO_3$ solution was added (pH~7–8). The resulting mixture was extracted with EtOAc, dried over $Na_2SO_4$ and the solvent was removed under reduced pressure. Chromatography ($SiO_2$ Type-H, 5% MeOH in $CH_2Cl_2$) of the residue yielded the title compound as a yellow gum (0.066 g, 0.25 mmol, 75% yield);

$^1H$ NMR ($CDCl_3$) δ 7.15 (m, 2H), 6.97 (d, 1H, J=6.9 Hz), 6.83 (br, s, 1H), 6.68 (d, 1H, J=8.1 Hz), 6.59 (d, 1H, J=8.1 Hz), 6.01 (d, 1H, J=1.4 Hz), 5.91 (d, 1H, J=1.4 Hz), 4.40–4.00 (m, 5H), 3.55 (dd, 1H, J=17.7, 3.0 Hz), 3.10 (t, 1H, J=12.0 Hz);

$^{13}C$ NMR ($CDCl_3$) δ 146.1, 144.8, 136.0, 132.2, 130.4, 128.6, 127.1, 127.0, 124.5, 118.5, 116.2, 106.2, 101.2, 45.8, 35.1, 34.3, and 28.9.

Anal. Calcd. for $C_{17}H_{15}NO_2 \cdot 0.52HCN \cdot 1.8H_2O$: C, 67.49; H, 6.18; N, 6.83. Found: C, 67.45; H, 5.96; N, 6.75.

Method B:

12H-Benzo[d,e][1,3]benzodioxol[4,5-h]isoquinoline (11.26 g) was dissolved into 500 mL of glacial acetic acid in a suitable glass liner that will fit into a 1-L Parr "bomb reactor." To this dark amber solution was added 480 mg $PtO_2$ and a magnetic stirring bar. Usual purge cycles were repeated three times at −78° C. Finally hydrogen gas was charged into the steel bomb at 140 PSI while the content was still at −78° C. The reactor was allowed to warm to room temperature over a period of 2 hours while the internal pressure increased to 195 PSI. Gas absorption was faster after about 4 hours at room temperature. After 24 hours, the internal pressure returned to 165 PSI indicating roughly stoichiometric uptake of hydrogen gas. The black suspension was removed after the pressure was relieved, filtered over silica gel, rinsed with acetic acid, and concentrated under reduced pressure to give about 19 gm of gummy substance. The crude product was neutralized with sodium bicarbonate solution followed by extraction with methylene chloride to yield 11.6 gm of the title compound whose 1H NMR was indistinguishable from the purified material prepared above by the Method A.

EXAMPLE 7

(±)-8,9-Dihydroxy-2,3,7,11b-tetrahydro-1H-napht[1,2,3-de]isoquinoline $BBr_3$ (25.0 mL of 1 M in $CH_2Cl_2$, 25.0 mmol) was added to a cooled solution (−78° C.) of methylenedioxy dinapsoline as prepared in Example 6 (1.4 g, 5.3 mmol) in $CH_2Cl_2$. The mixture was stirred at −78° C. under nitrogen for three hours and then at room temperature overnight. After the mixture was cooled to −78° C., methanol (50 mL) was added dropwise and the solvent was removed by reduced pressure. The residue was dissolved in methanol (100 mL) and the solution was refluxed under nitrogen for 2 hours. After removal of solvent, chromatography ($SiO_2$, 10% MeOH in $CH_2Cl_2$) of the residue yielded the title compound as a dark brown solid (1.65 g, 4.94 mmol, 93% yield). MS (ESI) m/z 254 ($MH^+$);

$^1H$ NMR (DMSO-$d_6$) δ 9.50 (br, s, 2H), 9.28 (s, 1H), 8.54 (s, 1H), 7.32 (d, 1H, J=8.3 Hz); 7.23 (t, 1H, J=8.3 Hz), 7.12 (d, 1H, J=8.5 Hz), 6.70 (d, 1H, J=9.3 Hz), 6.54 (d, 1H, J=6.7 Hz), 4.37 (s 2H), 4.30–4.23 (m, 2H), 3.97 (m, 1H), 3.45–3.31 (m, 2H);

$^{13}C$ NMR (DMSO-$d_6$) δ 143.8, 142.0, 136.9, 132.1, 127.6, 127.0, 126.6, 124.1, 123.7, 114.0, 112.7, 46.6, 44.0, 32.9, and 28.5.

Anal. Calcd. for $C_{16}H_{15}NO_2 \cdot 1.28HBr \cdot 0.59H_2O$: C, 52.34; H, 4.79; N, 3.82. Found: C, 52.29; H, 4.92; N, 4:14.

EXAMPLE 8

R-(+)-8,9-Dihydroxy-2,3,7,11b-tetrahydro-1H-napht[1,2,3-de]isoquinoline

Step A. (+)-8,9-Methylenedioxy-2,3,7,11b-tetrahydro-1H-napht[1,2,3-de]isoquinoline A sample of racemic (±)-8,9-methylenedioxy-2,3,7,11b-tetrahydro-1H-napht[1,2,3-de]isoquinoline was injected into a preparative HPLC (Dynamax Rainin Model SD-1) equipped with Chiralcel OD column (5 cm×50 cm, 20μ, Chiral Technologies, Inc) at a flow rate of 50 mL/min using V detector set at λ=220 nm. Using an isocratic method, the solvent system (5% Ethanol/Hexanes, 0.1% TFA) was found to best separate the enantiomers. As much as 150 mg/5 mL ethanol can be injected to the column per run. A total of 425 mg of racemic (±)-8,9-methylenedioxy-2,3,7,11b-tetrahydro-1H-napht[1,2,3-de]isoquinoline injected can produce about 200 mg of each enantiomer. Optical rotation was taken for each of the enantiomer collected:

$1^{st}$ Peak (Rf=19.6 minutes): $[\alpha]_D$ −88.9° (c 0.03, $CHCl_3$)

$2^{nd}$ Peak (Rf=23.6 minutes): $[\alpha]_D$ −90.3° (c 0.03, $CHCl_3$)

One of these two isomers was derivatized into the corresponding N-(p-tolylsulfonamide) for a single crystal X-ray determination. From there it was concluded that the chirality of the (−)-isomer of Formula VIIb has (S)-configuration at the asymmetric center. The second peak is the desired title compound.

Step B. R-(+)-8,9-Dihydroxy-2,3,7,11b-tetrahydro-1H-napht[1,2,3-de]isoquinoline

Using the identical deprotection procedure described for the racemic compound in Example 7, each of these isomers were subjected to $BBr_3$ deprotection to give chiral (+) and (−)-isomers of dinapsolines (DNS).

|  | DNS from first peak | DNS from second peak |
|---|---|---|
| Optical rotations $[\alpha]_D$ | −70.7° (c 0.03, MeOH) | +75.0° (c 0.03, MeOH) |

EXAMPLE 9

(R)-(+)-8,9-Dihydroxy-2,3,7,11b-tetrahydro-1H-napth[1,2,3-de]isoquinoline

Step A. (±)-8,9-Methylenedioxy-2,3,7,11b-tetrahydro-1H-napth[1,2,3-de]isoquinoline A solution of racemic (±)-8,9-methylenedioxy-2,3,7,11b-tetrahydro-1H-napth[1,2,3-de]isoquinoline (3.0 gm, 11.3 mmol) in 100 mL of 95% ethyl alcohol at room temperature was mixed with a warm solution of (+)-dibenzoyl-D-tartaric acid in 40 mL of 95% ethyl alcohol. The solution was allowed to stand at room temperature for 4 hours and the grayish off-white crystals were collected by filtration and subsequently dried in a vacuum oven at 35° C. to give 1.3 gm (melting point: 175–176° C., 35.7%). The enantiomeric purity was determined by the same chiral HPLC conditions described above in Example 8: the salt was neutralized with 2M potassium hydroxide solution and the organic materials extracted with methylene chloride. The organic layers were combined and concentrated under reduced pressure to give a white solid which was redissolved in methanol prior to injection into HPLC Chiral column. The ratio of the second peak to the first was determined to be greater than 40:1. The identical resolution may also be carried out using the unnatural D-tartaric acid. Melting points are uncorrected for the desired tartaric salts of the title compound.

(R)-(+)-(+)-8,9-methylenedioxy-2,3,7,11b-tetrahydro-1H-napth[1,2,3-de]isoquinoline (+)-dibenzoyl-D-tartaric Acid Salt:. mp 175–176° C.

(R)-(+)-(+)-8,9-methylenedioxy-2,3,7,11b-tetrahydro-1H-napth[1,2,3-de]isoquinoline D-tartaric Acid Salt: mp 186–188° C.; $[\alpha]^{25}$=+90.30°

Step B. (R)-(+)-8,9-dihydroxy-2,3,7,11b-tetrahydro-1H-napth[1,2,3-de]isoquinoline The free base is regenerated from the tartaric salts by neutralization. The (+)-isomer of dinapsoline prepared by deprotection as described in Example 7 is identical to the (+)-isomer of Example 8.

The invention claimed is:

1. A compound which is (R)-(+)-8,9-dihydroxy-2,3,7,11b-tetrahydro-1H-napth[1,2,3-de]isoquinoline or a nontoxic pharmaceutically acceptable salt thereof, the compound (R)-(+)-8,9-dihydroxy-2,3,7,11b-tetrahydro-1H-napth[1,2,3-de]isoquinoline provided in substantially pure form.

2. A pharmaceutical composition for the treatment of movement disorders, the composition comprising a therapeutically effective amount of a compound as defined in claim 1 in association with a nontoxic pharmaceutically acceptable carrier or diluent.

3. A method for the treatment of movement disorders in a mammal in need thereof, the method comprising administering to said mammal a therapeutically effective amount of a compound as defined in claim 1.

4. The method of claim 3 wherein the disorder is Parkinson's Disease.

* * * * *